US006699404B2

(12) United States Patent
Speronello et al.

(10) Patent No.: US 6,699,404 B2
(45) Date of Patent: Mar. 2, 2004

(54) MASSIVE BODIES CONTAINING FREE HALOGEN SOURCE FOR PRODUCING HIGHLY CONVERTED SOLUTIONS OF CHLORINE DIOXIDE

(75) Inventors: Barry K. Speronello, Montgomery Township, NJ (US); Gerald S. Koermer, Roseland, NJ (US); Appadurai Thangaraj, Edison, NJ (US); Ahmad Moini, Princeton, NJ (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 10/173,224

(22) Filed: Jun. 17, 2002

(65) Prior Publication Data

US 2003/0080317 A1 May 1, 2003

Related U.S. Application Data

(63) Continuation-in-part of application No. 09/496,803, filed on Feb. 2, 2000, now Pat. No. 6,432,322.

(51) Int. Cl.⁷ .......................... C01B 11/10; C01B 11/06
(52) U.S. Cl. ........................ 252/187.23; 252/187.21; 252/187.34; 252/186.35; 252/186.21; 423/477
(58) Field of Search ................... 252/187.23, 187.34, 252/186.21, 186.35, 187.21; 423/477

(56) References Cited

U.S. PATENT DOCUMENTS

| 2,071,094 A | 2/1937 | Vincent ..................... 167/17 |
| 4,104,190 A | 8/1978 | Hartshorn ............... 252/187 R |
| 4,547,381 A | 10/1985 | Mason et al. ............... 426/316 |
| 4,689,169 A | 8/1987 | Mason et al. .......... 252/186.24 |
| 5,324,447 A | 6/1994 | Lam et al. .............. 252/187.21 |
| 5,399,288 A | 3/1995 | Marzouk ............... 252/186.21 |
| 5,719,100 A | 2/1998 | Zahradnik et al. .......... 502/417 |
| 6,007,735 A | 12/1999 | Creed .................... 252/166.25 |
| 6,197,215 B1 | 3/2001 | Pitochelli ............... 252/187.21 |
| 6,238,643 B1 | 5/2001 | Thangaraj et al. .......... 423/477 |
| 6,294,510 B1 | 9/2001 | Norman et al. ............. 510/191 |

FOREIGN PATENT DOCUMENTS

| DE | 27 12 574 A | * 10/1977 |
| EP | 581 550 A | * 2/1994 |
| GB | 608068 | 9/1948 |
| WO | WO 99/24356 | * 5/1999 |
| WO | WO 99/62817 | * 12/1999 |

* cited by examiner

Primary Examiner—Joseph D. Anthony
(74) Attorney, Agent, or Firm—Russell G. Lindenfeldar

(57) ABSTRACT

A massive body, e.g., a tablet, for producing a solution of chlorine dioxide when the massive body is added to liquid water. The massive body comprises a metal chlorite such as sodium chlorite, an acid source such as sodium bisulfate and a source of free halogen such as the sodium salt of dichloroisocyanuric acid or a hydrate thereof. The concentration of free halogen in the solution will be:

(a) less than the concentration of chlorine dioxide in said solution on a weight basis and the ratio of the concentration of chlorine dioxide to the sum of the concentrations of chlorine dioxide and chlorite anion in said solution is at least 0.25:1 by weight; or (b) equal to or greater than the concentration of chlorine dioxide in said solution on a weight basis and the ratio of the concentration of chlorine dioxide to the sum of the concentrations of chlorine dioxide and chlorite anion in said solution is at least 0.50:1 by weight.

37 Claims, No Drawings

US 6,699,404 B2

MASSIVE BODIES CONTAINING FREE HALOGEN SOURCE FOR PRODUCING HIGHLY CONVERTED SOLUTIONS OF CHLORINE DIOXIDE

REFERENCE TO RELATED APPLICATION

This application is a continuation-in-part of application Ser. No. 09/496,803 filed Feb. 2, 2000 now U.S. Pat No. 6,432,322.

BACKGROUND OF THE INVENTION

Free molecular chlorine dioxide in solution is an effective agent for the control of microorganisms and biological film deposits. However, the most common way to produce such solutions of free chlorine dioxide is to use an expensive and complicated chemical generator (see for example U.S. Pat. No. 5,009,875).

British patent 608,068 teaches the use of organic acid anhydrides to convert chlorite anion to free chlorine dioxide at a generally neutral pH. The fire and explosion dangers that result from combining a strong oxidizing chemical, such as sodium chlorite, with an organic chemical are also well known. As a result of the low conversion ratio produced by the compositions of this British patent, and the dangers inherent in compositions combining sodium chlorite and organic chemicals, the compositions of this British patent have received little commercial interest.

Recently, a membrane-type device containing powdered chlorine dioxide precursor chemicals that produce a solution of free molecular chlorine dioxide when the device is immersed in water was described, see WO 99/24356. While this membrane device is superior to the prior art methods of producing chlorine dioxide solutions, the device has some shortcomings. It is relatively expensive (due to the cost of the membrane and of assembly), and the rate of chlorine dioxide delivery can be too slow for certain applications. Also, the device may float on the surface of the water/solution (due to entrapped air or chlorine dioxide gas), and this can result in the loss of some chlorine dioxide to the gas phase. Finally, the preferred membranes are insoluble in water, and may need to be removed from the chlorine dioxide solution after the chlorine dioxide generating reactions are completed. Removal of the spent membrane from the chlorine dioxide solution may, at times, be considered inconvenient.

The prior art also describes attempts to produce chlorine dioxide solutions from solid mixtures, including solid compacts such as tablets and briquettes, that are comprised of materials that will generate chlorine dioxide gas when contacted with liquid water.

U.S. Pat. No. 2,071,094 discloses dry solid compositions, including briquettes, comprised of a soluble chlorite and an acidifying agent that when contacted with water produce a "deodorizing reaction" as the dry composition begins to dissolve (see col. 1, lines 34–38 and col. 2, lines 24–27) Upon reading this patent, it is not clear what is produced when the composition comes into contact with water. The substance, chlorine dioxide, is never mentioned and the only time the word "solution" is used, it is with reference to an aqueous solution of sodium chlorite (see col. 1, line 58). Thus, it cannot be ascertained whether the inventor was attempting to, or indeed ever did, obtain an aqueous solution of chlorine dioxide when his briquette was contacted with water.

U.S. Pat. No. 4,104,190 describes tablets comprising sodium chlorite, a halogen-based activator and a buffer. The tablets may further comprise an acid. The preferred halogen-based activator is sodium dichloroisocyanuric acid. The conversion efficiency reported in the patent for the tablets is, for the most part, low. Ten of the examples in the '190 patent report sufficient data from which it is possible to calculate the chlorine dioxide and chlorite yields. Only two of those examples resulted in a rate of conversion of chlorite to chlorine near or above the minimum of 25% associated with the present invention. The maximum rate of conversion of chlorite to chlorine disclosed in the '190 patent was 37%. The concentration of chlorine produced by the tablets was not disclosed in the '190 patent, but experiments we have carried out have resulted in the conclusion that at the level of near or above 25% conversion of chlorite to chlorine dioxide, undesirably high concentrations of chlorine in solution were also produced. In one of the two examples of the '190 patent, the concentration of chlorine in the product solution was over double that of the concentration of chlorine dioxide in the solution. In the other example of the '190 patent, the concentration of chlorine in the product solution was over four times that of the concentration of chlorine dioxide in the solution.

Since chlorine dioxide is often used because it provides a biocidal function without many of the disadvantages of chlorine, it would desirable to develop a device to produce a highly converted solution of chlorine dioxide that did not also contain excessive amounts of chlorine. It would also be desirable to develop a device that produced a solution of chlorine dioxide where the conversion of chlorite to chlorine dioxide was greater than 37%.

U.S. Pat. No. 5,324,447 describes, inter alia, a tablet comprising a chlorine dioxide precursor (e.g., sodium chlorite) and an activator component (e.g., an organic acid anhydride) that are present in amounts effective to produce (contact) lens disinfecting amounts of chlorine dioxide in a liquid medium (see, col. 3, lines 10–16). The term "disinfecting amount" is defined as such amount as will reduce the microbial burden by one log order preferably in ten (10) minutes or less (see col. 4, lines 11–15). This amount represents very little free chlorine dioxide, as even as little as 2 ppm of free chlorine dioxide can result in a 6 log bacterial reduction in 15 minutes. The patent does not disclose the amount of chlorine dioxide that is generated when a tablet of the invention is dissolved in water. Thus, all of the examples utilize aqueous solutions of stabilized chlorine dioxide and not water to test the tablets.

U.S. Pat. No. 5,399,288 discloses a solid composition releasing chlorine dioxide immediately after dissolution in water (see col. 1, lines 5–7). The composition comprises a chlorite salt, an oxidizing chlorine-releasing agent and a proton donor present in the ratio of 4:1:3 (see col. 1, lines 65–67). When the oxidizing chlorine-releasing agent is omitted from the composition, the final yield of chlorine dioxide obtained was 63% but after three days (see Example 5). Further, and importantly, this patent does not discuss the preparation of tablets (see col. 2, lines 19–21). Thus, it appears that only powdered mixtures of reactants are disclosed.

U.S. Pat. No. 5,719,100 discloses production of chlorine dioxide in an aqueous solution from a tablet comprising a composition of sodium chlorite and an acid activator wherein the composition requires a reaction-preventing barrier between the sodium chlorite, i.e., a protective reactive coat is formed on the sodium chlorite before it is mixed with the acid activator (see col. 4, lines 61–63) and the acid activator such that the two active ingredients do not "explosively react" together prematurely (see col. 4, line 53), i.e., a stable composition is obtained (see col. 4, line 46 through col. 5, line 9).

The present invention provides an improved device in the form of a massive body for the production of chlorine dioxide solutions. This new device rapidly provides high yield solutions of chlorine dioxide and overcomes shortcomings of prior art solid compositions for producing such solutions.

DESCRIPTION OF THE INVENTION

This invention provides a massive body that rapidly produces a solution of chlorine dioxide when immersed in liquid water. The invention also includes the solutions obtained when the massive body is immersed in liquid water. As used herein, the term "massive body" means a solid shape, preferably a porous solid shape, comprising a mixture of granular particulate ingredients wherein the size of the particles comprising the ingredients is substantially smaller than the size of the massive body. Such massive bodies may be formed by a variety of means known in the art, such as tableting, briquetting, extrusion, sintering, granulating and the like. The preferred method of forming such massive bodies is by compression, also known as tableting. For reasons of convenience, hereinafter references to tablets and tableting shall be understood to be representative of massive bodies made by any method.

The massive body comprises a metal chlorite, an acid source and a source of free halogen. The massive body is such that when it is added to liquid water, it will produce a solution of chlorine dioxide and free halogen, with the concentration of free halogen in the solution being:

(a) less than the concentration of chlorine dioxide in the solution on a weight basis and the ratio of the concentration of chlorine dioxide to the sum of the concentrations of chlorine dioxide and chlorite anion in the solution is at least 0.25:1 by weight; or (b) equal to or greater than the concentration of chlorine dioxide in the solution on a weight basis and the ratio of the concentration of chlorine dioxide to the sum of the concentrations of chlorine dioxide and chlorite anion in the solution is at least 0.50:1 by weight.

The metal chlorite comprises an alkali or alkaline earth metal chlorite, preferably sodium chlorite that may be utilized in a technical grade. Suitable acid sources include inorganic acid salts, such as sodium acid sulfate, potassium acid sulfate, sodium dihydrogen phosphate, and potassium dihydrogen phosphate; salts comprising the anions of strong acids and cations of weak bases, such as aluminum chloride, aluminum nitrate, cerium nitrate, and iron sulfate; acids that can liberate protons into solution when contacted with water, for example, a mixture of the acid ion exchanged form of molecular sieve ETS-10 (see U.S. Pat. No. 4,853,202) and sodium chloride; organic acids, such as citric acid and tartaric acid; and mixtures thereof. Preferably, the acid source is an inorganic acid source, and most preferably is sodium bisulfate.

Suitable examples of the free halogen source include dichloroisocyanuric acid and salts thereof such as sodium dichloroisocyanurate and/or the dihydrate thereof (alternatively referred to as the sodium salt of dichloroisocyanuric acid and/or the dihydrate thereof and hereinafter collectively referred to as "NaDCCA"), trichlorocyanuric acid, salts of hypochlorous acid such as sodium, potassium and calcium hypochlorite, bromochlorodimethylhydantoin, dibromodimethylhydantoin and the like. The preferred source of the free halogen is NaDCCA.

Surprisingly, a very high conversion rate of the chlorite anion to chlorine dioxide is obtained by use of the tablets of the invention. Thus, when the equivalent weights of tablet ingredients in powdered form are added to the same volume of water as the corresponding tablet, a much larger amount of chlorine dioxide is produced by the tablet than from the powder. Reasonable variations in stirring rate and/or water temperature have little to no effect on this surprising phenomenon.

Although not wishing to be bound by theoretical considerations, it is believed that the very high conversion rate of chlorite anion to chlorine dioxide resulting from the use of the tablets of the present invention occurs because the tablets either contain or develop a pore structure. Such pore structure facilitates the penetration of water therein, thereby dissolving reagents into solution within the pores and producing advantageous conditions for the conversion of chlorite anion to chlorine dioxide within the pores.

It is known in the art that the rate of the reaction wherein chlorite anion is converted to chlorine dioxide under acidic conditions is of a very high order in both the concentration of chlorite anion and acidity. Increasing those concentrations dramatically increases the rate of chlorine dioxide formation.

It is believed that when water penetrates into the pore structure of the tablet, the water dissolves soluble constituents from the tablet and thereby forms a substantially saturated acidic solution of chlorite anion within the pores. Accordingly, the conversion rate of chlorite anion to chlorine dioxide is high. Nevertheless, despite the high rate of chlorine dioxide formation, a pore network must remain intact for a sufficient period of time to allow the conversion reaction to proceed to the desired degree. Once the reagents have dissolved into solution, the further conversion of chlorite anion to chlorine dioxide is very small.

The pore size and pore volume ranges required to facilitate the desired degree of conversion of chlorite anion to chlorine dioxide will depend upon many factors, e.g., the particular combination of reagents in the tablet, the size of the tablet, the shape of the tablet, the temperature of the water, other chemicals dissolved in the water, the desired degree of conversion of chlorite anion to chlorine dioxide, the desired amount of free halogen to be delivered into the solution, etc. Accordingly, it is not believed that there is a single optimum range of pore sizes or pore volumes that will produce an optimum result.

It is within the capability of one skilled in the art to vary the pore size and the pore volume of a tablet to achieve the desired result in respect to the characteristics of the chlorine dioxide solution. For example, the pore size and pore volume may be varied by varying the particle size of the powder used to prepare the tablet or by varying the compaction force used to form the tablet or by varying both the particle size and the compaction force. Larger particles of powder will generally produce larger pores and more pores in the tablet. Increasing compaction force will generally reduce both the size and volume of the pores in the tablet.

The tablets of the invention have been observed to rapidly produce a highly converted solution of free molecular chlorine dioxide, meaning that the conversion ratio (chlorite anion to chlorine dioxide) is 0.25 or above. Preferably, the conversion ratio is at least 0.50, more preferably at least 0.60, and most preferably at least 0.75. The term "conversion ratio", when utilized herein, means the calculated ratio of the free chlorine dioxide concentration in the product solution to the sum of free chlorine dioxide plus chlorite ion concentrations in the product solution. Further, the chlorine dioxide solution is rapidly produced in a safe and controlled manner; and when the chlorine dioxide concentration so produced is at typical use levels (about 0.1 to about 1,000 ppm, preferably about 0.5 to about 200 ppm, by weight) in typical tap water, the solution will contain substantially no free chlorine or other free halogen and will have a generally neutral pH By the term "rapidly produced", we mean that total chlorine dioxide production is obtained in less than about 8 hours, preferably in less than about 2 hours and most preferably in less than about 1 hour. By the term "no free chlorine or other free halogen", we mean that the concentration of free chlorine or other free halogen in solution is less than the concentration of chlorine dioxide in said solution on a weight basis, preferably less than ½ the concentration of chlorine dioxide in said solution, more preferably less than ¼ the concentration of chlorine dioxide, and most preferably no more than ¹⁄₁₀ the concentration of chlorine dioxide, on a weight basis.

By the term, "generally neutral pH", we mean that the pH is higher than that normally required to form substantial concentrations of free chlorine dioxide in solution (i.e., pH higher than about 2) and lower than the pH at which chlorine dioxide is known to disproportionate in solution (i.e., pH below about 12). Preferably, the pH of the resultant solution is between about 4 and 9 to minimize the potential for corrosion of materials with which the solution comes into contact. More preferably the pH of the resultant solution should be in the range of about 5–9, and most preferably in the range of about 6–9; ideally the pH will be 7. In certain cases, it may be advantageous to produce chlorine dioxide in a solution that is already at either a higher or a lower pH than the pH of about 7. Tablets of the invention may be used to deliver chlorine dioxide into such solutions without materially changing the pH of the solution when the chlorine dioxide concentration is at typical use levels. For example, if a tablet of the invention is used to produce chlorine dioxide in a typical solution of laundry detergent, it is advantageous for the detergent solution to be at alkaline pH (i.e., >9) where the detergent functions best. Tablets of the invention may be used for that purpose. In such cases, however, it is preferred that the pH of the resultant detergent/chlorine dioxide solution be below about 12, as chlorine dioxide degrades at a pH higher than about 12.

It is advantageous for the free halogen concentration of the resultant solution to be low, as free halogen can lead to corrosion of materials in which the solution comes into contact, and free halogen can react with organic materials to produce toxic halogenated hydrocarbons. Because of the ability of tablets of the invention to produce highly converted solutions of chlorine dioxide in the absence of a halogen source, it is possible to use sufficiently low amounts of a free halogen source in the tablet formulation to accelerate the chlorine dioxide formation reaction without contributing excessive amounts of free halogen to the resultant solution.

In other situations, the presence of a relatively high concentration of chlorine or other free halogen in solution may be acceptable. In such situations, it is possible to use the massive bodies of the invention to produce very highly converted aqueous solutions of chlorine dioxide where the ratio of the concentration of chlorine dioxide in solution to the sum of the concentrations of chlorine dioxide and chlorite anion is greater than 0.5 on a weight basis. In those cases, the concentration of chlorine or free halogen in solution may be equal to or even greater than the concentration of chlorine dioxide in solution on a weight basis.

The tablets of the present invention may, if desired, contain optional additional ingredients, that may be useful, for example, to assist in the tableting process, to improve the physical or aesthetic characteristics of the produced tablets and to assist tablet solubilization and/or the yield of chlorine dioxide obtained. Such ingredients include but are not limited to fillers such as attapulgite clay and sodium chloride; tableting and tablet die lubricants; stabilizers; dyes; anti-caking agents; desiccating filling agents such as calcium chloride and magnesium chloride; pore forming agents such as a swelling inorganic clay, e.g., Laponite clay available from Southern Clay Products, Inc., and a framework former that can react with one or more other constituents in the formulation to produce a low solubility porous framework structure in which the chlorine dioxide forming reactions may proceed.

Effervescing agents such as sodium bicarbonate may be included in small amounts, e.g., about 1 to about 50 wt. %, based on the weight of the massive body, but they can reduce the conversion of chlorite anion to chlorine dioxide by accelerating breakup and dissolution of the tablet.

In general the tablets of the invention are superior to the prior art membrane device, see e.g., WO 99/24356, for the following reasons:

Tablets are typically less costly than the membrane device because they can be manufactured at a high rate on commercially available equipment and do not require the expense of a membrane enclosure to function;

Tablets generally produce chlorine dioxide at a higher rate than membrane devices, since the tablet does not have a membrane to restrict the escape of chlorine dioxide into solution;

The membrane devices frequently float when they are added to water while the tablets of the invention sink in water so little chlorine dioxide is lost to the gas phase; and In one preferred mode, the tablet of the invention is completely soluble in water so the need to remove residue from the product chlorine dioxide solution is avoided.

While not wishing to be bound by any theory of operation, we believe that the enhanced yield of chlorine dioxide that is obtained by the use of the tablets of the invention may be explained in the following way. The tablet device functions when water enters the pore space within a tablet and produces a concentrated, acidic solution of chlorite anion within the pore space. The acid and chlorite (and optional ingredients that may be present) react under these concentrated conditions in the pores of the tablet rapidly to produce chlorine dioxide that diffuses out of the tablet into the bulk solution.

For the tablets to function properly, it is believed important that the chemical reactions occur in concentrated solution within the pore structure. There is little or no chlorine dioxide formed when the equivalent tablet ingredients in powder form are rapidly dissolved in aqueous media.

The invention includes two general types of tablet devices. One type of device comprises tablets that are filly soluble in water, and the preferred formulation of such tablets comprises dried powdered technical grade sodium chlorite and a dried powdered acid source, preferably sodium bisulfate. Additional dried powdered ingredients such as magnesium chloride may optionally be added to even further improve the yield and rate of production of the chlorine dioxide. The dried powdered ingredients are mixed and the resultant powdered mixture is compressed in a tablet die at a force sufficient to produce a substantially intact tablet, typically about 1000–10,000 lb./in$^2$.

The resultant tablets are stable during storage as long as they are protected from exposure to water (either liquid or vapor). The tablets rapidly produce a highly converted solution of free chlorine dioxide when immersed in water.

The second type of device comprises tablets, that are not fully soluble in water at a high rate. They are designed to have (or produce) a low solubility or slowly soluble porous framework structure in which the chlorine dioxide forming reactions may proceed to substantial completion prior to dissolution of the porous framework. Generally tablets of this second type convert a greater proportion of their chlorite anion precursor chemical to chlorine dioxide compared to the fully soluble tablets described above.

The preferred formulation for this second type of tablet device comprises dry powdered sodium chlorite, dry powdered sodium bisulfate and dry powdered calcium chloride. A dry powdered clay such as Laponite clay may optionally be added to even further improve the yield and rate of production of the chlorine dioxide. As with tablets of the first type, the dry powdered ingredients are mixed and the resultant powdered mixture is compressed in a tablet die at a force sufficient to produce a substantially intact tablet, typically about 1000–10,000 lb./in$^2$. The resultant tablets are stable during storage as long as they are protected from exposure to water (either liquid or vapor). They rapidly produce a highly converted solution of free chlorine dioxide when immersed in water.

Tablets of this second type generally provide more efficient conversion of chlorite anion to chlorine dioxide compared to tablets of the first type. It is believed that this occurs because the low solubility porous framework provides a favorable environment for the chlorine dioxide forming reactions to proceed until substantial exhaustion of the reactants.

Chlorine dioxide formation in tablets of the second type of device is believed to occur substantially within the favorable environment of the pore space of the low solubility (or slowly soluble) porous framework. Since the favorable pore structure of this framework appears to remain substantially intact during this reaction time, substantially all of the chlorite anion has an opportunity to react and form chlorine dioxide under favorable conditions within the pores. This maximizes chlorite conversion to chlorine dioxide. In contrast, a device of the first type is being dissolved into the bulk solution at the same time that it is producing chlorine dioxide. Since it is believed that the reagents will only react at a practically useful rate under concentrated conditions (such as those that exist within the pores of the tablets), that fraction of the chlorite that dissolves into bulk solution prior to conversion to chlorine dioxide will substantially remain as chlorite and not be converted to chlorine dioxide under the generally dilute conditions of the bulk solution.

The low solubility porous framework of the preferred composition of the second type of tablet device comprises a framework former such as a low solubility compound such as calcium sulfate, calcium phosphate, aluminum phosphate, magnesium phosphate, ferric sulfate, ferric phosphate or zinc phosphate; or a low solubility amorphous material such as silica-alumina gel, silica-magnesia gel, silica-zirconia gel, or silica gel; and may additionally include a clay or other substantially insoluble framework or pore former such as Laponite clay. The calcium sulfate preferably is formed from the reaction between calcium cations e.g., from the calcium chloride constituent and sulfate anions derived from the sodium bisulfate constituent. Other sources of calcium cations such as calcium nitrate as well as other sources of sulfate anions such as magnesium sulfate may also be used. Phosphate anion preferably is provided by use of soluble phosphate compounds such as sodium phosphate, sodium hydrogen phosphate, sodium dihydrogen phosphate, the corresponding potassium phosphate salts, as well as other soluble phosphate salts. The silica alumina gel preferably is formed from the reaction between sodium silicate and aluminum sulfate. Silica-magnesia gel preferably is formed from the reaction between sodium silicate and magnesium sulfate. Silica-zirconia gel preferably is formed from the reaction between sodium silicate and zirconyl sulfate. Silica gel preferably is formed from the reaction between sodium silicate and acidity from the solid acid source. Additional solid acid component may be required to compensate for the alkalinity of the sodium silicate constituent.

The preferred clay, Laponite clay, is insoluble as provided and it is a swelling clay that, we believe, enhances the pore structure of the porous framework by forming cracks and cavities as it swells. We have found that forming the low solubility porous framework, e.g., the calcium sulfate, calcium phosphate, aluminum phosphate, etc., frameworks in-situ via chemical reaction is particularly advantageous and that the chlorine dioxide yield from tablets wherein the framework is formed in-situ is significantly better (nominally 25% better) than tablets in which the framework material is a constituent of the initial powder formulation. The presence of the clay in addition to the framework material provides only a small improvement over the use of the framework material, without the clay.

By the term "low solubility or slowly soluble porous framework", we mean a porous solid structure that remains substantially undissolved in the product solution during the period of chlorine dioxide production. It is not necessary that the porous framework remain wholly intact during the reaction time to form chlorine dioxide. One aspect of this invention includes tablets of the second type in which the tablet disintegrates into substantially insoluble (or slowly soluble) granules that release chlorine dioxide into solution. This is acceptable, we believe, because the size of the granules is still large relative to the size of the pores within the pore space of the granules, so the necessary concentrated reaction conditions exist within the pore space despite the breakdown of the framework into granules. Typically, the framework former will be present in an amount of about 10 to about 90 wt. %, based on the weight of the massive body.

In tablet devices of both types, it is preferred that the powdered ingredients be dry prior to mixing and tableting in order to minimize premature chemical interaction among the tablet ingredients. When utilized herein, the term "dry" means that each ingredient typically contains less than about 1% water.

General Procedures for Making and Testing the Tablets of the Invention

Tablet Formation

The individual chemical components of the tablet formulation are dried prior to use. The desired amount of each component is carefully weighed into a plastic vial. In the following examples, formulations are given on a weight percent basis. The vial containing all the components of the tablet formulation is shaken to mix the components thoroughly. The contents of the vial are emptied into an appropriately sized die (e.g., a 13-mm diameter for a 1 g tablet). The plunger is placed in the die and the contents are pressed into a pellet using a hydraulic laboratory press. The maximum force reading on the press gauge was 2000 pounds unless otherwise noted. This force on the tablet punch may be converted to pounds/in$^2$ if the area of the face of the plunger in in$^2$ is known (typically 0.206 in$^2$ for a 1 g tablet). The resulting tablet is removed from the die and placed in a closed plastic vial until use (typically within 10 minutes).

Tablet Performance:

The tablet is placed in a volumetric flask or container filled with a known amount of tap water. Chlorine dioxide evolution starts immediately as evidenced by bubbles and the appearance of a yellow color. The tablet is allowed to react until completion. Completion of the reaction depends, in part, on the tablet type and size. Typically the reaction time is 2 hours or less if a 1 g tablet is partially insoluble and 0.5 hr. if a 1 g tablet is completely soluble. When reaction is complete, the flask/container is shaken or stirred in order to mix the contents. Then the contents are analyzed. Typically, chlorine dioxide is measured by uv-vis spectrometry, using four wavelengths (the average value is reported). Chlorite and chlorine are measured by titration of typically 25 ml of chlorine dioxide solution using procedures equivalent to those found in the text, *Standard Methods for the Examination of Water and Wastewater*, 19$^{th}$ Edition (1995) pages 4–57 and 4–58. This text is published jointly by the American Public Health Association, The American Water Works Association and the Water Environment Federation. The publication office is American Public Health Association, Washington, D.C. 20005. Total oxidants are measured by titration using a Brinkmann Autotitration System, 716 DMS Titrino equipped with a massive platinum electrode (Brinkmann Part No. 6.0415.100). The method is an iodimetric titration in an acid medium based on the oxidation of iodide to iodine and its subsequent reaction with the titrant, sodium thiosulfate. The typical procedure was as follows. One hundred milliliters of chlorine dioxide solution and a stirring bar were placed in a beaker and 2 g of potassium iodide (Reagent Crystals) and 10 ml of a 1N solution of sulfuric acid (Mallinckrodt) were added with stirring. The resulting solution is titrated with 0.1N thiosulfate solution (Aldrich Chemical Co.). The endpoint is automatically determined by the Brinkmann Titrino software. This endpoint is used to calculate the concentration of total oxidants in the sample. The pH of the original chlorine dioxide solution is measured using a pH electrode either on the solution "as is" and/or diluted with sufficient water to give approximately a 10 ppm concentration of chlorine dioxide.

Results:

In the examples below, the above procedures are followed unless otherwise specified. Formulations are given as weight percent of each component on a dry basis. Technical grade sodium chlorite was used. Typically the actual sodium chlorite content of technical grade sodium chlorite is approximately 80% and the remainder is approximately sodium chloride (8.5%), sodium carbonate (6.1%) and sodium sulfate (4.5%). Yields are calculated on two bases. The first is the wt. % yield of chlorine dioxide based on the tablet weight, i.e., wt. % yield=100×(wt.ClO$_2$/wt. tablet). The second is the chemical yield based on sodium chlorite. In this case one must take into account that technical grade sodium chlorite is only 80% pure. Thus, chemical % yield= 100×(moles ClO$_2$ produced)/(moles of NaClO$_2$ in tablet). The stoichiometry of the acid reaction of sodium chlorite to chlorine dioxide limits the yield to 80%.

Conversion ratio is calculated as (wt. chlorine dioxide)/ (wt. chlorine dioxide+wt. chlorite). If the chlorite content of the solution was not determined or is unknown, a "minimum conversion ratio" is calculated. This ratio is wtClO$_2$/wt. total oxidant. Total oxidant typically consists entirely of chlorine dioxide, chlorite and chlorine. The chlorine content of solutions from tablets is typically low, so this minimum conversion ratio is a reasonable approximation of the conversion ratio. The examples are illustrated below.

EXAMPLE 1

Three one-gram tablets were made with the following composition:

| Sodium Chlorite | 38% |
|---|---|
| Dichloroisocyanuric acid, sodium salt | 9 |
| Sodium Bisulfate | 35 |
| Calcium Chloride | 18 |

The tablets were made at 3000 lb. force. Each tablet was placed in three liters of tap water for two hours with the following results.

|  | A | B | C |
|---|---|---|---|
| ClO$_2$ ppm | 47.5 | 46.9 | 47.0 |
| Total Oxidant (ppm) | 58.7 | 58.0 | 53.2 |
| pH | 6.8 | 6.8 | 6.8 |
| Wt. % Yield | 14.3 | 14.1 | 14.1 |
| Chemical % Yield | 63 | 62 | 62 |
| Conversion Ratio* | 0.81 | 0.81 | 0.88 |

*Minimum ratio; ppm ClO$_2$/ppm total oxidant

EXAMPLE 2

A one-gram tablet was made with the following composition:

| Sodium Chlorite | 37% |
|---|---|
| Dichloroisocyanuric acid, sodium salt | 15 |
| Sodium Bisulfate | 30 |
| Calcium Chloride | 18 |

The tablet was made at 2000 lb. force. The tablet was placed in three liters of tap water for 2.5 hours with the following results.

| ClO$_2$ ppm | 49.8 |
|---|---|
| Total Oxidant ppm | 69.7 |
| pH | 6.6 |
| Wt. % Yield | 14.9 |
| Chemical % Yield | 68 |
| Conversion ratio* | 0.71 |

*Minimum ratio; ppm ClO$_2$/ppm total oxidant

EXAMPLE 3

Two one-gram tablets were made with the following composition:

| Sodium Chlorite | 7% |
|---|---|
| Dichloroisocyanuric acid, sodium salt | 1 |
| Sodium Bisulfate | 12 |
| Calcium Chloride | 48 |

-continued

| | |
|---|---|
| Sodium Chloride | 16 |
| Sodium Sulfate | 16 |

The tablets were made at 2000 lb. force. Each tablet was placed in 0.5 liters of tap water for 1 hour with the following results.

| | A | B |
|---|---|---|
| $ClO_2$ ppm | 57.4 | 58.0 |
| Chlorite ppm | 4.3 | 6.1 |
| Chlorine ppm | 2.2 | 2.2 |
| pH (10 ppm) | 6.76 | 6.77 |
| Wt. % Yield | 2.87 | 2.90 |
| Chemical % Yield | 69 | 69 |
| Conversion ratio | 0.93 | 0.90 |

EXAMPLE 4

Two one-gram tablets were made with the following composition:

| | |
|---|---|
| Sodium Chlorite | 7% |
| Dichloroisocyanuric acid, sodium salt | 1 |
| Sodium Bisulfate | 12 |
| Sodium Chloride | 40 |
| Sodium Sulfate | 40 |

The tablets were made at 2000 lb. force. Each tablet was placed in 0.5 liters of tap water for 0.5 hour with the following results.

| | A | B |
|---|---|---|
| $ClO_2$ ppm | 53 | 54.8 |
| Chlorite ppm | 7.6 | 41 |
| Chlorine ppm | 0.1 | 1.2 |
| pH (10 ppm) | 7.41 | 7.36 |
| Wt. % Yield | 2.65 | 2.74 |
| Chemical % Yield | 63 | 66 |
| Conversion ratio | 0.87 | 0.93 |

EXAMPLE 5

Two one-gram tablets were made with the following composition:

| | |
|---|---|
| Sodium Chlorite | 26% |
| Dichloroisocyanuric acid, sodium salt | 7 |
| Sodium Bisulfate | 26 |
| Sodium Chloride | 20 |
| Magnesium Chloride | 21 |

The tablets were made at 2000 lb. force. Each tablet was placed in 1.0 liter of tap water for 0.25 hour with the following results.

| | A | B |
|---|---|---|
| $ClO_2$ ppm | 104.2 | 105.1 |
| Total Oxidant ppm | 115.3 | 109.7 |
| pH | 6.47 | 6.52 |
| Wt. % Yield | 10.42 | 10.51 |
| Chemical % Yield | 67 | 68 |
| Conversion ratio* | 0.90 | 0.96 |

*Minimum ratio; ppm $ClO_2$/ppm total oxidant

EXAMPLE 6

A one-gram tablet was made with the following composition:

| | |
|---|---|
| Sodium Chlorite | 34% |
| Dichloroisocyanuric acid, sodium salt | 8 |
| Sodium Bisulfate | 26 |
| Sodium Chloride | 16 |
| Magnesium Chloride | 16 |

The tablet was made at 2000 lb. force. The tablet was placed in 1.0 liter of tap water for 0.25 hour with the following results

| | |
|---|---|
| $ClO_2$ ppm | 123.3 |
| Total Oxidant ppm | 144.4 |
| pH | 6.47 |
| Wt. % Yield | 12.3 |
| Chemical % Yield | 61 |
| Conversion ratio* | 0.85 |

*Minimum ratio; ppm $ClO_2$/ppm total oxidant

EXAMPLE 7

This example illustrates the efficacy of generating chlorine dioxide by using a tablet as opposed to powder. Two one-gram samples of the following formulation were prepared.

| | |
|---|---|
| Sodium Chlorite | 25% |
| Sodium Dichloroisocyanurate | 8 |
| Sodium Bisulfate | 31 |
| Calcium Chloride | 31 |
| Laponite | 5 |

One sample was left as a mixed powder. The other sample was pressed into a tablet using 2000 pounds force. Each sample was placed in ten liters of water that was stirred using a paddle stirrer. The results after 1.5 hours indicated that the yield of chlorine dioxide from the tablet was an order of magnitude greater than that from the equivalent powder.

| | Tablet | Powder |
|---|---|---|
| $ClO_2$ ppm | 8.8 | 0.75 |
| Total Oxidant ppm | 12.0 | 14.5 |
| pH | 7.20 | 7.18 |

-continued

|  | Tablet | Powder |
|---|---|---|
| Wt. % Yield | 8.8 | 0.8 |
| Chemical % Yield | 59 | 5 |
| Conversion ratio* | 0.73 | 0.05 |

*Minimum ratio; ppm $ClO_2$/ppm total oxidant

EXAMPLE 8

This example shows that it is better to form calcium chloride in-situ in the tablet than to add calcium sulfate to the tablet formulation.

The following formulations were made into tablets using 6000 lb. force. The tablets were placed into 1 liter of tap water. After 3 hours, the resulting solutions were analyzed.

|  | A | B |
|---|---|---|
| Sodium Chlorite (T) (g) | 0.30 | 0.30 |
| Sodium Dichloroisocyanurate (g) | 0.10 | 0.10 |
| Sodium Bisulfate (g) | 0.30 | 0.30 |
| Calcium Chloride (g) | 0.25 |  |
| Calcium Sulfate (g) |  | 0.25 |
| Laponite (g) | 0.05 | 0.05 |
| Total (g) | 1.00 | 1.00 |

Results:

|  | A | B |
|---|---|---|
| $ClO_2$ ppm | 124.0 | 96.0 |
| Total Oxidant ppm | 133.0 | 120.3 |
| pH | 6.7 | 6.2 |
| Wt. % Yield | 12.4 | 9.6 |
| Chemical % Yield | 69 | 54 |
| Conversion ratio* | 0.93 | 0.80 |

*Minimum ratio: ppm $ClO_2$/ppm total oxidant

EXAMPLE 9

A one-gram tablet was prepared from the following formulation using 6000 lb. force:
0.167 g Sodium Chlorite Technical
0.500 g Sodium Bisulfate
0.330 g Sodium Chloride The tablet was placed in 1 liter of tap water and analyzed after 10 minutes (all components soluble).

| Results: | |
|---|---|
| $ClO_2$ ppm | 40 |
| Total Oxidant ppm | 48.6 |
| pH | 3.6 |
| Wt. % Yield | 4 |
| Chemical % Yield | 40 |
| Conversion ratio* | 82 |

*Minimum ratio; ppm $ClO_2$/ppm total oxidant

EXAMPLE 10

Three tablets of varying size were prepared from a single formulation as shown below. The tablets were placed in enough tap water so the final concentration of chlorine dioxide would be 100–200 ppm. Since larger tablets take more time to release chlorine dioxide, the reaction time was adjusted (as shown) to insure that sampling occurred when reaction was complete. Different dies were used to press the tablets such that the height/diameter ratios for the tablets were substantially equivalent and the force used to press the tablets was approximately the same on a force/unit cross sectional area basis.

|  | A | B | C |
|---|---|---|---|
| $NaClO_2$ (T) (g) | 0.38 | 4.22 | 34.2 |
| Na Dichloroisocyanurate (g) | 0.09 | 1.00 | 8.10 |
| Sodium Bisulfate (g) | 0.35 | 3.89 | 31.5 |
| Calcium Chloride (g) | 0.18 | 2.00 | 16.2 |
| Total (g) | 1.00 | 11.11 | 90.0 |
| Tablet Force (lb.) | 2000 | 6000 | 20000 |
| Volume (Liters) | 1 | 10 | 120 |
| Reaction Time (h) | 1.0 | 2.0 | 7.0 |

Results are shown below:

|  | A | B | C |
|---|---|---|---|
| $ClO_2$ ppm | 139.8 | 161.9 | 103.2 |
| Total Oxidant ppm | 159.0 | 169.1 |  |
| Chlorite ppm |  |  | 15.93 |
| Chlorine ppm |  |  | 5.34 |
| pH (@ 10 ppm) | 6.7 | 7.1 | 7.3 |
| Wt. % Yield | 14.0 | 14.6 | 13.8 |
| Chemical % Yield | 62 | 64 | 61 |
| Conversion ratio | 88* | 96* | 87 |

*Minimum ratio; ppm $ClO_2$/ppm total oxidant

EXAMPLE 11

Three tablets of varying size were prepared from a single formulation as shown below. The tablets were placed in enough tap water so the final concentration of chlorine dioxide would be 100–200 ppm. Since larger tablets take more time to release chlorine dioxide, the reaction time was adjusted (as shown). Sampling occurred when reaction was complete, i.e., after the tablet dissolved. Different dies were used to press the tablets such that the height/diameter ratios for the tablets were substantially equivalent and the force used to press the tablets was approximately the same on a force/unit cross sectional area basis.

|  | A | B | C |
|---|---|---|---|
| $NaClO_2$ (T) (g) | 0.26 | 2.886 | 23.14 |
| Na Dichloroisocyanurate (g) | 0.07 | 0.777 | 6.23 |
| Sodium Bisulfate (g) | 0.26 | 2.886 | 23.14 |
| Magnesium Chloride (g) | 0.21 | 2.331 | 18.69 |
| Sodium Chloride (g) | 0.20 | 2.220 | 17.80 |
| Total (g) | 1.00 | 11.10 | 89.00 |
| Pressure (lb.) | 2000 | 6000 | 20000 |
| Volume (L) | 1 | 10 | 121.4 |
| Reaction Time (h) | 0.25 | 0.5 | 1.0 |

The results are shown below:

|  | A | B | C |
|---|---|---|---|
| ClO$_2$ ppm | 97.9 | 111.1 | 64.7 |
| Total Oxidant ppm | 120.6 | 132.8 | 86.5 |
| pH | 7.6 | 7.7 | 7.0 |
| Wt % Yield | 9.8 | 10.0 | 8.8 |
| Chemical % Yield | 63 | 65 | 57 |
| Conversion ratio* | 0.81 | 0.84 | 0.75 |

*Minimum ratio; ppm ClO$_2$/ppm total oxidant

EXAMPLE 12

Various solids were added to the tablet formulation to determine if there was benefit from having these insoluble solids in the tablet. Tablet pressure was 6000 lb. unless noted. Reaction times were generally as long as the tablet still bubbled (released gas). The generic formulation for the tablets is shown below:

| Sodium Chlorite (T) (g) | 0.1 |
|---|---|
| Sodium Chloride (g) | 0.2 |
| Sodium Bisulfate (g) | 0.3 |
| Additive (g) | 0.4 |
| Total (g) | 1.0 |

One-gram tablets were placed in 1 liter of tap water. Results are shown below:

| Additive | Na Laponite | H+ Laponite | ETS-10 | Silica Gel |
|---|---|---|---|---|
| ClO$_2$ ppm | 37.4 | 38.1 | 13.9 | 20.5 |
| Total Oxidant ppm | 46.5 | 49.3 | 16.2 | 22.5 |
| pH | 6.7 | 6.4 |  |  |
| Reaction Time |  |  | 0.25 |  |
| Wt. % Yield | 3.7 | 3.8 | 1.6 | 2.1 |
| Chemical % Yield | 63 | 64 | 23 | 34 |
| Conversion Ratio* | 0.80 | 0.77 | 0.86 | 0.91 |

*Minimum ratio; ppm ClO$_2$/ppm total oxidant

| Additive | LaY | Veegum | Bentone | Attagel 40 |
|---|---|---|---|---|
| ClO$_2$ ppm | 18.1 | 20.1 | 29.9 | 25.1 |
| Total Oxidant ppm | 24.7 | 37.1 | 34.3 | 35.6 |
| pH |  | 6.3 | 6.3 |  |
| Reaction Time | 1 |  |  |  |
| Wt. % Yield | 1.8 | 2.0 | 3.0 | 2.5 |
| Chemical % Yield | 30 | 34 | 50 | 42 |
| Conversion Ratio* | 0.73 | 0.54 | 0.87 | 0.70 |

*Minimum ratio: ppm ClO$_2$/ppm total oxidant.

| Additive | Montmorillonite | Bentonite |
|---|---|---|
| ClO$_2$ ppm | 12.5 | 6.5 |
| Total Oxidant ppm | 25.6 | 23.8 |
| pH | 6.1 | 5.9 |
| Reaction Time |  |  |
| Wt. % Yield | 1.3 | 0.7 |
| Chemical % Yield | 21 | 11 |
| Conversion ratio* | 0.49 | 0.27 |

*Minimum ratio: ppm ClO$_2$/ppm total oxidant

What is claimed is:

1. A massive body comprising a metal chlorite, an acid source and a source of free halogen, said massive body being such that when it is added to liquid water, it sustains a pore structure that will produce a solution of chlorine dioxide and free halogen, the concentration of free halogen in said solution being:
    (a) less than the concentration of chlorine dioxide in said solution on a weight basis and the ratio of the concentration of chlorine dioxide to the sum of the concentrations of chlorine dioxide and chlorite anion in said solution is at least 0.25:1 by weight; or
    (b) equal to or greater than the concentration of chlorine dioxide in said solution on a weight basis and the ratio of the concentration of chlorine dioxide to the sum of the concentrations of chlorine dioxide and chlorite anion in said solution is at least 0.50:1 by weight.

2. The massive body of claim 1 wherein the concentration of free halogen in said solution is less than ½ of the concentration of chlorine dioxide in said solution on a weight basis and the ratio of the concentration of chlorine dioxide to the sum of the concentrations of chlorine dioxide and chlorite anion in said solution is at least 0.25:1 by weight.

3. The massive body of claim 1 wherein the concentration of free halogen in said solution is less than ¼ of the concentration of chlorine dioxide in said solution on a weight basis and the ratio of the concentration of chlorine dioxide to the sum of the concentrations of chlorine dioxide and chlorite anion in said solution is at least 0.25:1 by weight.

4. The massive body of claim 1 wherein the concentration of free halogen in said solution is less than 1/10 of the concentration of chlorine dioxide in said solution on a weight basis and the ratio of the concentration of chlorine dioxide to the sum of the concentrations of chlorine dioxide and chlorite anion in said solution is at least 0.25:1 by weight.

5. The massive body of claim 1 wherein the concentration of free halogen in said solution is equal to or up to about 100 times the concentration of chlorine dioxide in said solution on a weight basis and the ratio of the concentration of chlorine dioxide to the sum of the concentrations of chlorine dioxide and chlorite anion in said solution is at least 0.50:1 by weight.

6. The massive body of claim 1 wherein the ratio of the concentration of chlorine dioxide to the sum of the concentrations of chlorine dioxide and chlorite anion in said solution is at least 0.60:1 by weight.

7. The massive body of claim 1 wherein the ratio of the concentration of chlorine dioxide to the sum of the concentrations of chlorine dioxide and chlorite anion in said solution is at least 0.75:1 by weight.

8. The massive body of claim 1 which is completely soluble in water.

9. The massive body of claim 1 which does not completely dissolve in water.

10. The massive body of claim 1 which forms a low solubility porous framework when added to liquid water.

11. The massive body of claim 1 wherein the metal chlorite comprises sodium chlorite.

12. The massive body of claim 1 wherein the acid source comprises sodium bisulfate.

13. The massive body of claim 1 further comprising magnesium chloride.

14. The massive body of claim 1 wherein the source of free halogen comprises a material selected from the group consisting of dichloroisocyanuric acid, a salt of dichloroisocyanuric acid, a hydrated salt of dichloroisocyanuric acid, trichlorocyanurac acid, a salt of hypochlorous acid, bromochlorodimethylhydantoin and dibromodimethylhydantoin.

15. The massive body of claim 14 wherein the source of free halogen comprises the sodium salt of dichloroisocyanuric acid.

16. The massive body of claim 14 wherein the source of free halogen comprises the sodium salt of dichloroisocyanuric acid dihydrate.

17. The massive body of claim 1 further comprising a source of calcium ions.

18. The massive body of claim 17 wherein the source of calcium ions comprises calcium chloride.

19. The massive body of claim 1 further comprising agents that will form a low solubility porous framework when the massive body is added to liquid water.

20. The massive body of claim 19 wherein the low solubility porous framework is made up of calcium sulfate.

21. The massive body of claim 1 further comprising a swelling inorganic clay.

22. The massive body of claim 21 wherein the clay comprises Laponite clay.

23. The massive body of claim 1 wherein the concentration of chlorine dioxide in the solution is about 0.1 to about 1,000 ppm by weight.

24. The massive body of claim 23 wherein the concentration of chlorine dioxide in the solution is about 0.5 to about 500 ppm by weight.

25. The massive body of claim 1 wherein the total amount of chlorine dioxide in the solution is produced within a period of less than about 8 hours.

26. The massive body of claim 25 wherein the total amount of chlorine dioxide in the solution is produced within a period of less than about 2 hours.

27. The massive body of claim 26 wherein the total amount of chlorine dioxide in the solution is produced within a period of less than about 1 hour.

28. The massive body of claim 1 which produces a solution having a pH in the range of about 2 to about 12.

29. The massive body of claim 28 which produces a solution having a pH in the range of about 4 to about 9.

30. The massive body of claim 29 which produces a solution having a pH in the range of about 5 to about 9.

31. The massive body of claim 30 which produces a solution having a pH in the range of about 6 to about 9.

32. The massive body of claim 1 further comprising an effervescing agent.

33. The massive body of claim 32 wherein the effervescing agent is present in an amount of about 1 to about 50 wt. %, based on the weight of the massive body.

34. The massive body of claim 32 wherein the effervescing agent comprises sodium bicarbonate.

35. The massive body of claim 1 which comprises sodium chlorite, sodium bisulfate, calcium chloride and the sodium salt of dichloroisocyanuric acid dihydrate.

36. The massive body of claim 1 which comprises sodium chlorite, sodium bisulfate, magnesium chloride and the sodium salt of dichloroisocyanuric acid dihydrate.

37. The massive body of claim 1 which comprises sodium chlorite, sodium bisulfate, sodium bicarbonate, magnesium chloride and the sodium salt of dichloro-isocyanuric acid dihydrate.

* * * * *